United States Patent

Budd et al.

[11] Patent Number: 5,553,611
[45] Date of Patent: Sep. 10, 1996

[54] ENDOCARDIAL MEASUREMENT METHOD

[75] Inventors: Jeffrey R. Budd, St. Paul; John A. Hauck, Shoreview; Graydon E. Beatty, St. Paul, all of Minn.

[73] Assignee: Endocardial Solutions, Inc., St. Paul, Minn.

[21] Appl. No.: 376,067

[22] Filed: Jan. 20, 1995

Related U.S. Application Data

[63] Continuation of Ser. No. 178,128, Jan. 6, 1994, abandoned.

[51] Int. Cl.[6] .................................................. A61B 5/05
[52] U.S. Cl. ........................ 128/642; 128/693; 128/694; 128/734
[58] Field of Search .......................... 128/639, 641–2, 128/691–734; 607/122–3, 125–8

[56] References Cited

U.S. PATENT DOCUMENTS

| | | | |
|---|---|---|---|
| 4,380,237 | 4/1983 | Newbower | 128/693 |
| 4,572,206 | 2/1986 | Geddes et al. | 128/692 |
| 4,674,518 | 6/1987 | Salo | 128/695 |
| 4,721,115 | 1/1988 | Owens | 128/713 |
| 4,840,182 | 6/1989 | Carlson | 128/694 |
| 4,898,176 | 2/1990 | Petre | 128/642 |
| 4,911,174 | 3/1990 | Pederson et al. | 128/695 |
| 4,951,682 | 8/1990 | Petre | 128/713 |
| 5,000,190 | 3/1991 | Petre | 128/713 |
| 5,058,583 | 10/1991 | Geddes et al. | |
| 5,297,549 | 3/1994 | Beatty et al. | 128/642 |
| 5,311,866 | 5/1994 | Kagan et al. | 128/642 |

OTHER PUBLICATIONS

"Communications", Conductance Volumetric Model Of An Eccentrically Positioned Catheter Within A Three–Compartment Ellipsoidal Ventricle, by Steven Kun and Robert A. Peura, IEEE Transactions On Biomedical Engineering, vol. 40, No. 6, Jun., 1993.
"New Catheter Will Find And Treat Cardiac Arrhythmias".

*Primary Examiner*—Angela D. Sykes
*Attorney, Agent, or Firm*—Merchant, Gould, Smith, Edell, Welter & Schmidt, P.A.

[57] ABSTRACT

A collection of measurements are taken from a set of measurement electrodes to determine the position of a catheter in a heart chamber. The preferred measurement catheter includes a relatively large dielectric volume.

7 Claims, 6 Drawing Sheets

ENDOCARDIAL MEASUREMENT METHOD

CROSS-REFERENCE

This is a continuation of application Ser. No. 08/178,128 filed Jan. 6, 1994, now abandoned.

The present application is related to the subject matter of United States patent application Ser. No. 07/949,690, filed Sep. 23, 1992, issued on May 17, 1994 as U.S. Pat. No. 5,311,866, disclosing a heart mapping catheter; and United States patent application Ser. No. 07/950,448, filed Sep. 23, 1992, issued on Mar. 29, 1994 as U.S. Pat. No. 5,297,549, disclosing an electro-physiological mapping method.

TECHNICAL FIELD

The present invention relates generally to a method of making intra-cardiac measurements of distance based upon impedance data. This distance information can be used to determine the location of a measurement catheter within a heart chamber. The distance information can also be used to determine the volume of the heart chamber.

BACKGROUND ART

The interior volume of the heart can be measured or estimated in a number of ways. Radiographic dilution techniques and impedance plethysmography are two widely used techniques. Impedance measures have been used to extrude volume and have also been used as a feedback parameter for implantable pacemakers and for direct hemodynamic measurements in a diagnostic setting.

Traditionally impedance measurements have been made using catheters which employ multiple ring electrodes on the distal end of a catheter. Such methods use a widely spaced pair of current driving electrodes on an elongate cylindrical catheter shaft. Typically one or more pairs of ring electrodes for sensing the resultant voltages are also placed on the shaft. This catheter is placed in a heart chamber. The measured impedance has been found to be directly related to the total volume of the chamber in which the catheter is placed.

Kuhn (IEEE Transactions on Biomedical Engineering, Vol. 40 No. 6 June 1993 pp 589–592) determined the effects of catheter movement on measurements of volume based on impedance measurements. Using such calculations, Kuhn created a look-up table which enabled him to calculate chamber volume without regard to the position of the catheter.

Prior art volume estimation techniques do not measure provide a intracavitary distances which is a shortcoming of the prior art.

SUMMARY

The invention discloses a technique for determining the distance to the walls of a heart chamber from impedance measurements made with electrodes mounted on a mapping catheter.

In use, a pair of excitation electrodes generate an electric field in the heart chamber. Sets of measurement electrodes located on a relatively large insulator surface collect impedance data. The impedance data are highly directional and the measurements from all sets of measurement electrode sets are used to generate a distance measure in a so-called index direction. The index direction is sequentially incremented and a collection of distance measurements are constructed which collectively express the location of the mapping catheter within the heart chamber. In general, many of such measurement processes are completed within one heart cycle.

BRIEF DESCRIPTION OF THE DRAWINGS

The various figures of the drawing represent an illustrative embodiment of the invention, but it should be understood that many modifications to the invention may be made without departing from the scope of the invention. Throughout these drawings identical reference numerals refer to identical structure throughout in which.

DETAILED DESCRIPTION

Figure 1:
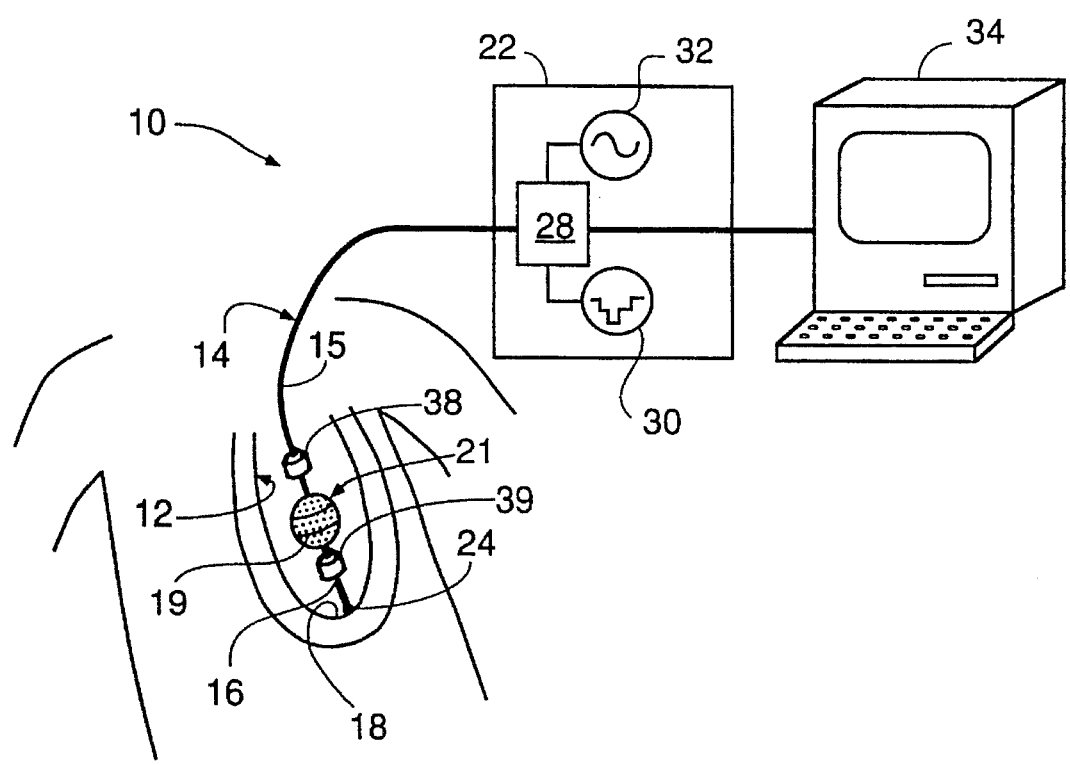
FIG. 1 is a schematic view of the system.

FIG. 1 is a schematic diagram depicting the impedance measurement system 10 in use. The impedance measurement system 10 includes a mapping catheter assembly 14 which is coupled to a signal interface assembly 22, which in turn, is coupled to a computer 34. The mapping catheter assembly is shown inserted into a patients heart chamber 12. The mapping catheter assembly 14 includes several sets of measurement electrodes located on a balloon 19, and a pair of excitation electrodes 38, 39 located on the catheter shaft 15 adjacent to the balloon 19.

The signal interface assembly 22 includes a signal generator 32 and an A to D convertor 30. The signal generator 32 generates the excitation pulses applied to the excitation electrode set while the A to D convertor 30 is used to digitize impedance measurements made at the various measurement electrode sites. The various electrodes are coupled to the signal generator 32 and A to D convertor 30 through a multiplexor 28. It is preferred to place the signal generator 32, the A to D convertor 30, and multiplexor 28 under software control executed by the computer 34.

The computer 34 is preferably of the "workstation" class to provide sufficient processing power to operate in essentially real time. This computer operates under the control of software set forth in the flow chart of FIG. 6.

Any of a variety of materials can be used for making the catheter assembly 14 and any of a variety of mechanical constructions can be used to form an acceptable mapping catheter without departing from the scope of the invention.

The principle elements of the mapping catheter assembly 14 are the elongate catheter shaft 15; the inflatable balloon 19; and the reference catheter extension 16. In general, the mapping catheter assembly 14 includes a wire braid formed of insulated wires. Insulation is removed from various wires in the braid to form "spot" electrodes which have a relatively small surface area. The inflatable balloon 19 lies behind the braid and when the balloon 19 is inflated, the spot electrodes are moved into positions on the surface of a sphere or other shape. Although the balloon 19 is shown in the figure as a spherical structure for simplicity, other shapes are useful as well. The spot electrodes are used as the measurement electrodes. A pair of ring electrodes form first excitation electrode 38 and second excition electrode 39. These electrodes are placed on the catheter shaft 15 and are used as the excitation electrodes for the system.

Figure 2:
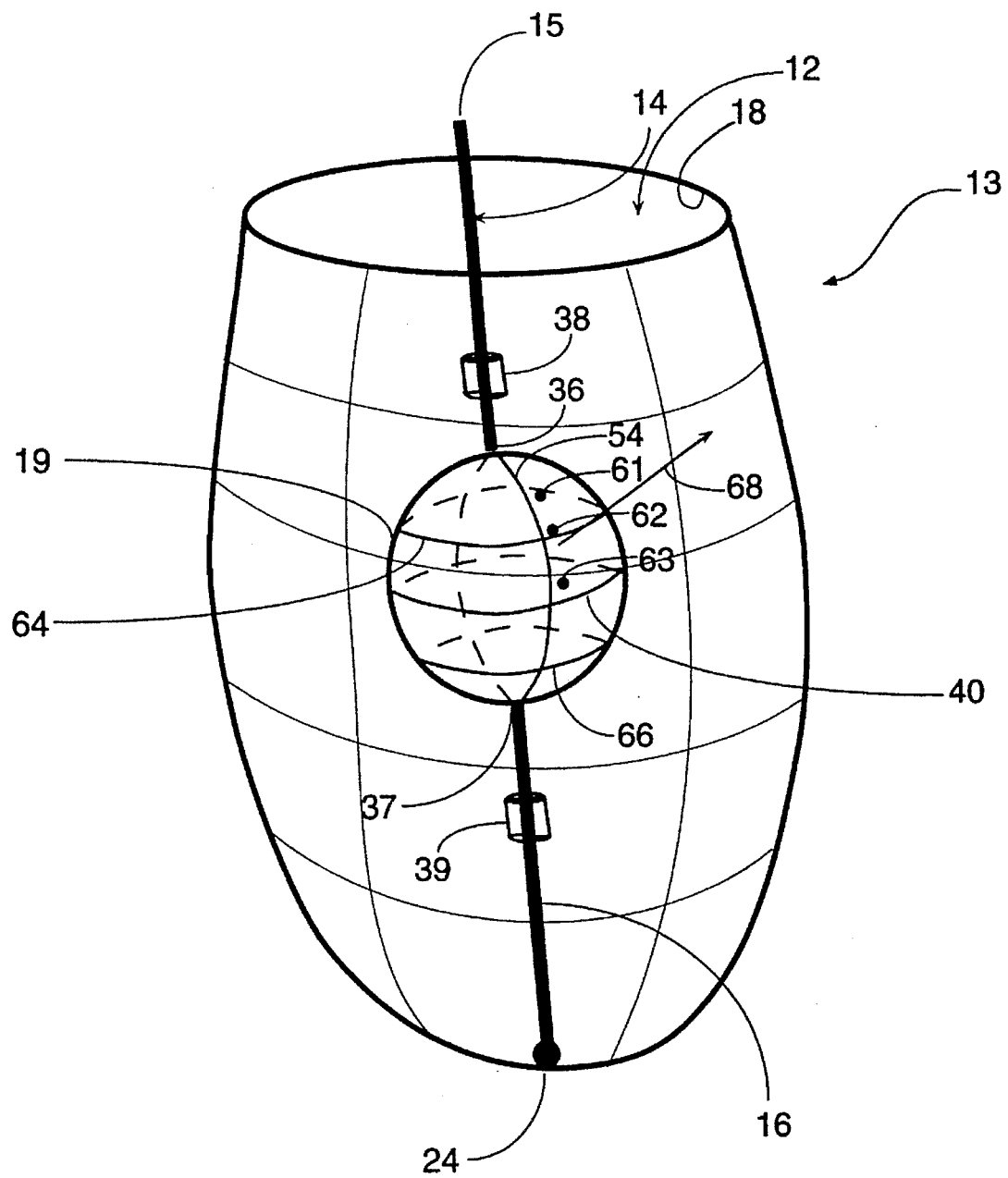
FIG. 2 is a schematic and perspective view representing the intra-cardiac probe.

FIG. 2 sets forth the geometry of the mapping catheter assembly 14 in more detail. This figure shows the mapping catheter assembly 14 inserted into a heart chamber 12. The wire grid 13 represents a volumetric rendition of the heart chamber taken from distance measurements. The distance measures used to form the grid can also be used to animate heart wall motion showing variations in wall movement.

The reference catheter 16 and catheter shaft 15 form an axis which define the poles 36, 37 for the spherical balloon 19. The first excitation electrode 38 is mounted on the catheter shaft 15 "above" the balloon 19 and second excitation electrode 39 is located "below" the balloon 19 on the catheter shaft 15. In use, an electric field is generated by the application of a voltage pulse between the first and second excitation electrodes. This field is affected by the location of the endocardial surface 18 and the electrical properties of the blood within the heart chamber 12. The inflatable balloon 19 excludes blood from a portion of the heart chamber 12 and thus distorts the applied field, confining it between the endocardial surface 18 and the balloon 19. The presence of the dielectric surface of the balloon also makes the spot electrodes very directional since they are bounded by non conductive materials and are presented with conductive blood on only one side.

Discussion of the measurement electrodes is facilitated by reference to a great circle or meridian 54; an equator 40; and "tropic" circles 64 and 66. Preferably the first or "upper" tropic circle 64 lies half way between the first pole 36 and the equator 40 while the second or "lower" tropic circle 66 is located halfway between the second pole 37 and the equator 40. The measurement electrode sets are preferably arrayed around these tropics. An exemplary set of measurement electrodes is shown in the figure as first electrode 61, second electrode 62 and third electrode 63. Preferably each of these electrodes lies on a single meridian so that each electrode is a different distance away from either pole. Preferably the "middle" or second electrode 62 is used as a reference for differential measurements made with the first electrode 61 and the third electrode 63. In general the measurement data taken with this exemplary electrode set of electrodes is directional and correlates to the direction 68 normal to the surface of the balloon 19. Several sets of measurement electrodes are arrayed around the upper tropic circle 64 and the lower tropic circle 66, however these sets are not shown to simplify FIG. 2.

Figure 3:
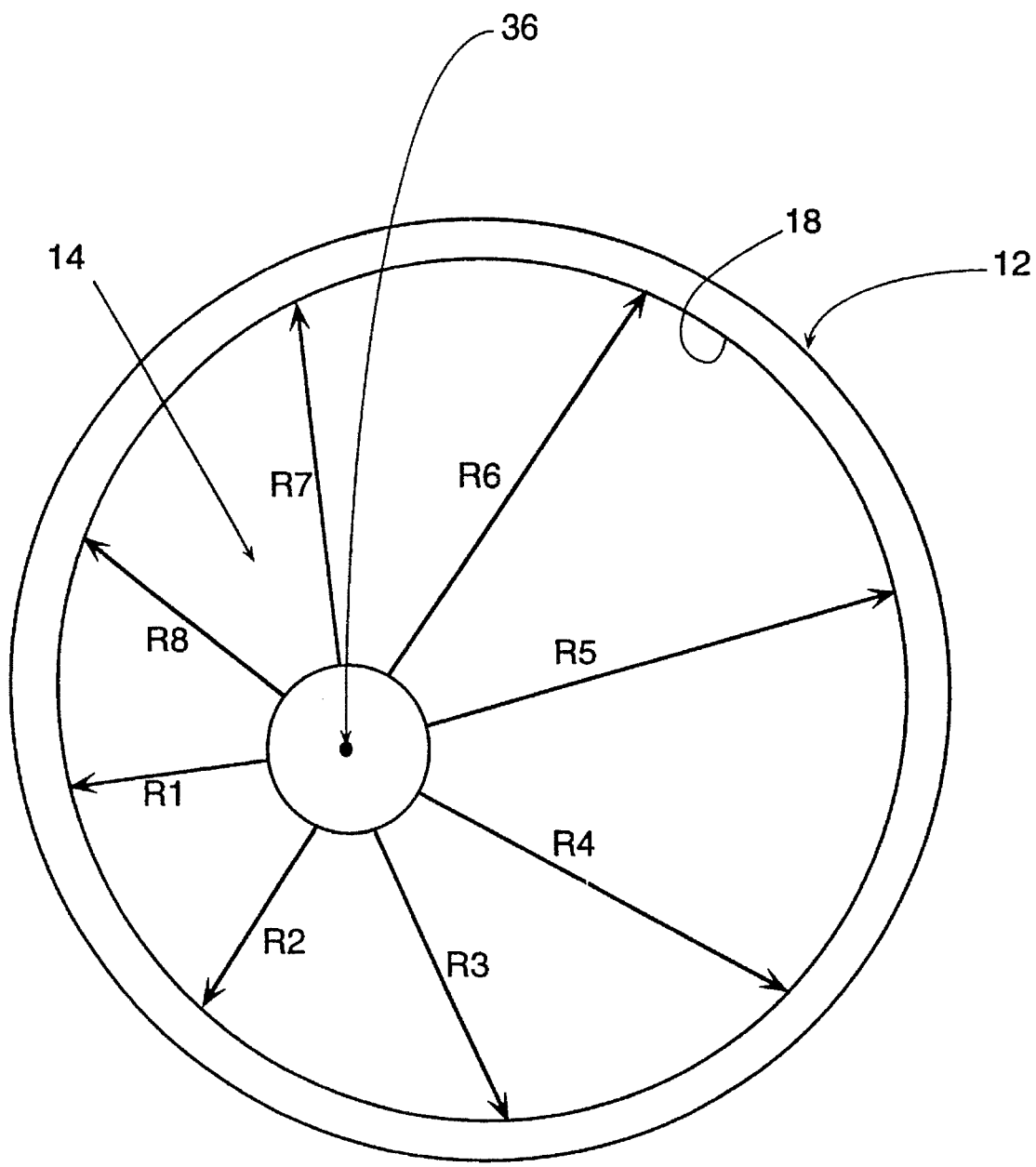
FIG. 3 is a schematic view representing the intra-cardiac distances measured with the probe.

FIG. 3 is a schematic cross section of a heart chamber 12 as seen from above. The pole 36 shows the location of the axis. Each "spoke" R1 through R8 in the figure is a vector quantity which represents both the viewing directions of independent sets of measurement electrodes located on the upper tropic 64 of the measuring catheter assembly 14 and the value of the resistance measurement in that direction. Thus the impedance measurements are also denominated by R1 through R8 in the drawing. In general, these measurements are collected virtually simultaneously. Qualitatively, the spokes R2 and R1 will have higher resistance values than spokes R5 and R6, because the associated measurement electrodes are closer to the endocardial surface 18.

Figure 4:
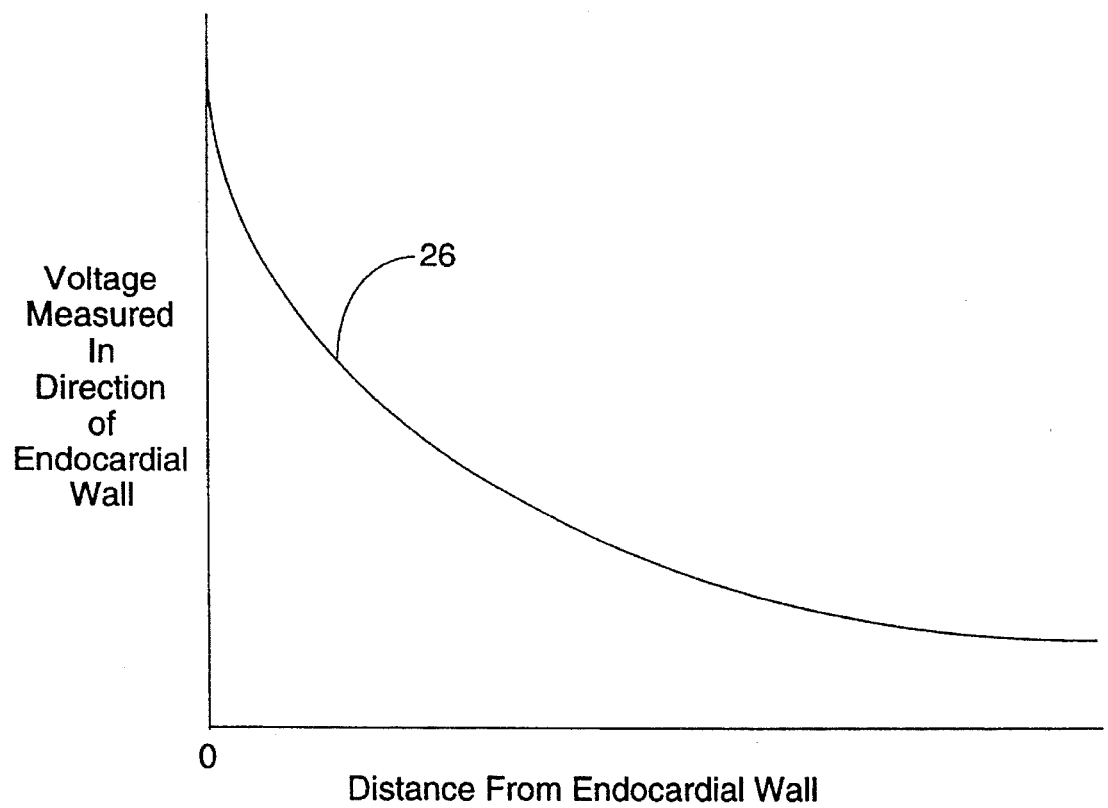
FIG. 4 describes the relationship between voltage measurements and distance to the heart chamber wall.

FIG. 4 shows a graph depicting the relationship between the measured impedance value expressed as a resistance and the distance from the endocardial wall. This empirically derived curve 26 can be used to develop the linearized expression set forth in the figure. This expression may be applied as follows. Take the spoke R1 as the index direction. The various empirically derived coefficients Cof1 through Cof9 are applied to each the appropriate impedance measures and used to compute the index distance referred to as D in the expression. Next the same expression is computed with another spoke taken as the index electrode set. The terms are additive and less than all the terms shown can be used to estimate the distance. The final multiplier of the expression, the ratio of the minimum resistance and the index resistance, may be regarded as a "concentricity coefficient" and it approaches unity as the mapping catheter assembly 14 is centralized in the heart. Other compensatory factors are preferably used as well.

Figure 5:
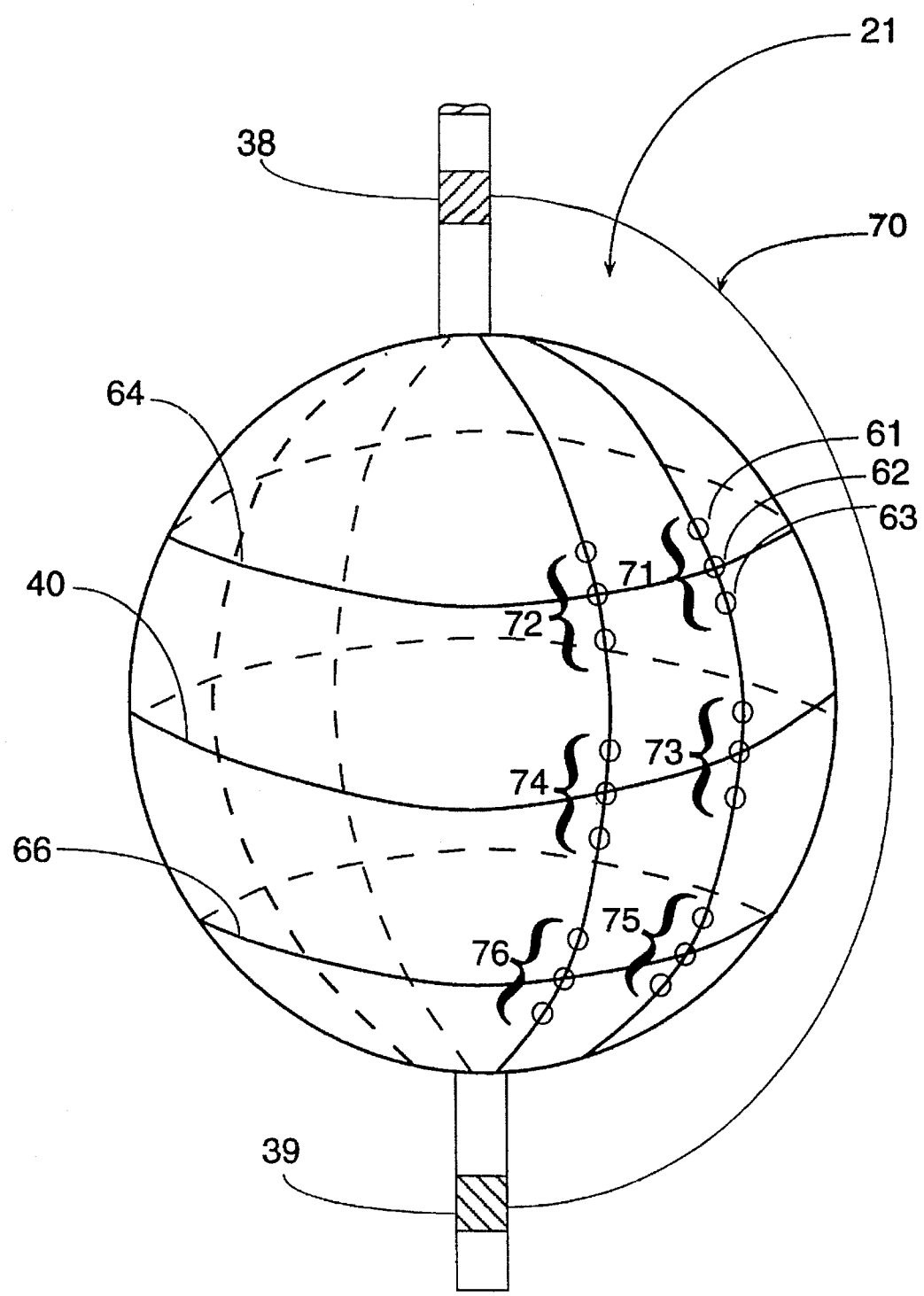
FIG. 5 is a schematic perspective view representing the electrode locations.

FIG. 5 shows six sets of measurement electrodes and two excitation electrodes. A single field line 70 is shown for simplicity. Consider the upper tropic circle 64 and specifically measurement electrode set 71. The differential measurement between electrode 61 and electrode 62 (Ra) should be essentially equal to the differential measurement between electrode 62 and 63 (Rb) since these two pairs are essentially the same distance from the endocardial surface 18. However there is a perceptible difference between these two measurements (Ra–Rb not equal 0) caused by the non uniformity of the field 70 as it arcs toward the excitation electrode 38. This non-linearity is accommodated by an expression in the form Rc=Rb–K*(Ra–Rb) where the compensation constant (K) is empirically determined. In general, the compensation constant (K) will be the same for all measurement electrodes at the same latitude. Consider equatorial measurement electrode set 73. For these electrodes the field uniformity should be at a maximum and disparities in the differential measurement made can be attributed to non-uniformities in blood conductivity. A compensation factor can be developed to remove errors due to this non-linearity. However in practice acceptable accuracy has been achieved with only sixteen "tropical" electrodes sets compensated for field non-uniformity.

EXAMPLE

A test probe was prepared with an ellipsoidal dielectric body having a major axis of 4 cm. and a minor axis of 1.6 cm. Each excitation electrode was located 7.5 mm from the poles of the ellipsoidal body. The measurement electrodes were placed on the tropical circles as described above. Empirically derived coefficient use to determine distance were: Cof1=–588.8; Cof2=270.9; Cof3=–42.0; Cof4=–8.3; Cof5=22.6; Cof6=–70.50; Cof7=76.9; Cof8=142.0; Cof9= 2.91. The field compensation constant was K=1.32.

Method Description

Figure 6:
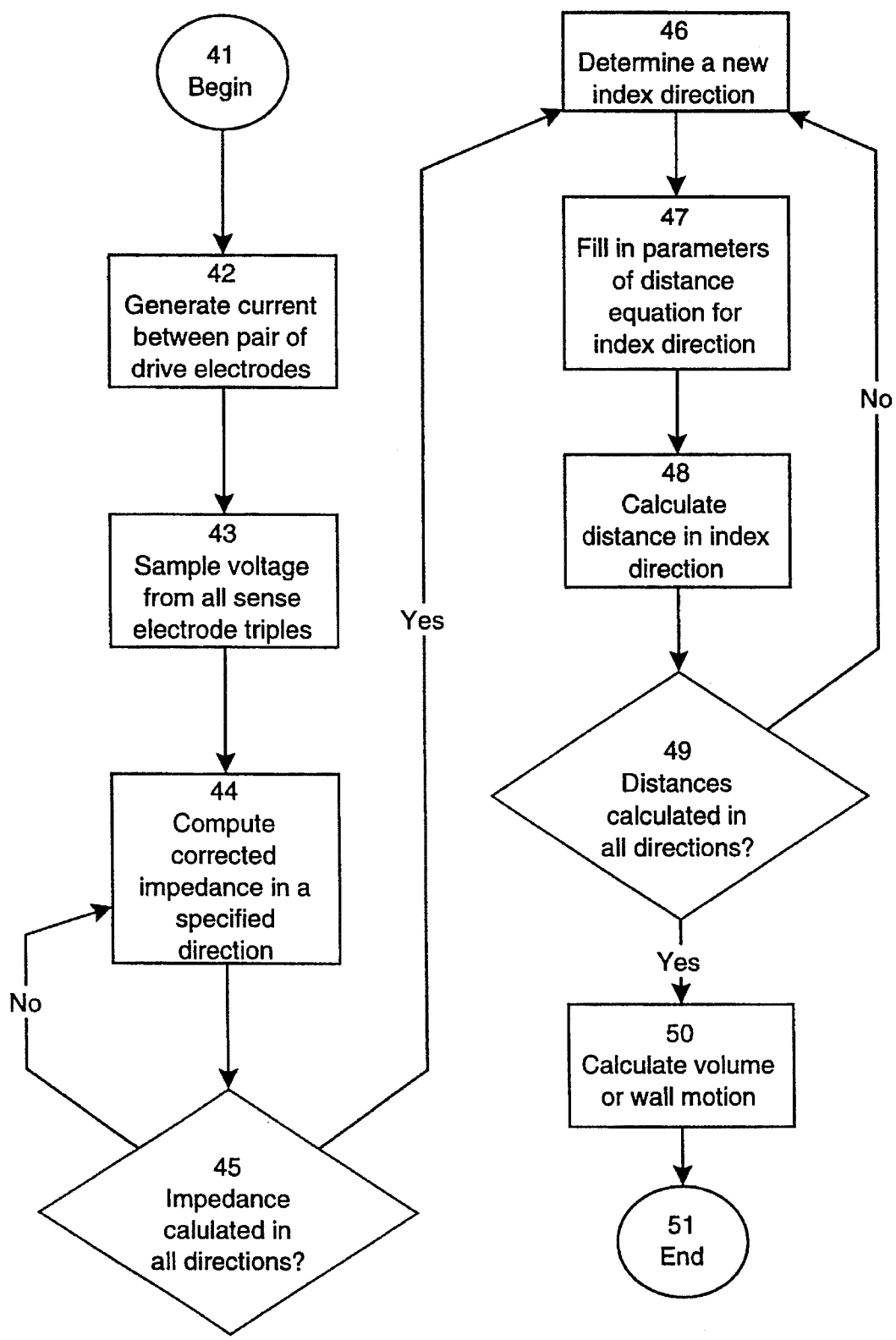
FIG. 6 is a schematic flow chart of illustrative steps for carrying out the method.

The illustrative method may be partitioned into 11 steps as shown in FIG. 6. The partitioning of the step-wise sequence is done as an aid to explaining the invention and other equivalent partitioning can be readily substituted without departing from the scope of invention.

The illustrative process assumes that the electrode array takes a known spherical or ellipsoidal shape within the heart chamber 12, and that there are at least twenty-four electrodes on the measurement electrode array 21. The location of each of these electrode sites on the array surface should be along meridians. If the reference catheter 16 is extended to the chamber wall 18 then its length can be used to measure distance to the distal wall of the heart chamber.

The process begins at step 41. In step 42, the current source electrode pair, 38 and 39, create an electrical field.

The measurement electrodes sense this field as a voltage. The more the field is impeded by the medium (blood) the higher the voltage. Since the endocardial tissue has approximately three times the impedance of blood, the impedance increases as the probe approaches the wall.

In step 43, the voltage is sampled at electrodes 61, 62 and 63 in a specific direction. In step 44, a correction is made for field non-uniformity as described above.

Once this corrected impedance measurement is made the process iterates at step 45. The loop between step 44 and 45 continues until the measured impedance in all directions is corrected for field non-uniformity.

Once this is done, a direction is determined, step 46, for measurement of distance between the probe and the chamber wall. First, in step 47, the parameters of the distance calculating equation from FIG. 4 are filled with measured impedances. Then, in step 48, the distance is calculated in the index direction. This series of steps between 46 and 49 loops until the distance in all directions is calculated.

If 8 columns of 3 longitudes are available on the electrode array 21 then 24 distance measurements will be determined in this fashion. If the extension of the reference catheter 16 to the reference location 24 is also used for a distance then 25 separate distance measurements are available.

In step 50, a three dimensional structure is fit to the individual directional distance measurements. This could be a cubic spline fit or other similar method. This model fit will give a three dimensional representation 80 of the geometry of the heart chamber wall 18 and the location within that structure of the electrode array 21. If desired, this three dimensional model 80 could be used to compute overall volume by standard integration techniques or to compute more specific information such as wall motion of selected areas of the endocardial wall 18. At this point, step 51, the routine ends or, if desired, another series of distance measures can be made to provide a continuous measure of chamber geometry.

We claim:

1. A method of measuring distance within the heart using a programmable data processing system, comprising data input means, display means, and data storage means, the method comprising the steps of:

(a) defining a blood exclusion volume within said heart;

(b) positioning a first excitation electrode and a second excitation electrode within said heart, proximate said blood exclusion volume such that said blood exclusion volume is between said first excitation electrode and said second excitation electrode;

(c) placing a first measurement set of electrodes within said heart proximate said blood exclusion volume, said first measurement set having at least a first electrode and a second electrode forming an index set of electrodes;

(d) placing a second measurement set of electrodes within said heart proximate said blood exclusion volume, said second measurement set having at least a third electrode and a fourth electrode, said first measurement set being opposed from said second measurement set;

(d) using the data input means to provide the programmable data processing system with data signals gathered from the first, second, third, and fourth electrodes;

(e) storing the data signals gathered from the first, second, third, and fourth electrodes in the data storage means; and (f) using the programmable data processing system to perform the steps of:

(1) measuring the impedance between said first and second electrodes forming a first resistance measurement (R1);

(2) measuring the impedance between said third and fourth electrodes forming a second resistance measurement (R2);

(3) applying a first empirically derived coefficient to said first resistance measurement, forming a first measure term;

(4) applying a second empirically derived coefficient to said second resistance measurement, forming a second measure term;

(5) combining said first measure term and said second measure term to determine the distance (D) to said wall from said index electrode set;

(6) displaying on the display means a value representing the distance (D) to said wall from said index electrode set.

2. The method of claim 1 wherein said first measurement set of electrodes lies on a meridian of said blood exclusion volume.

3. The method of claim 2 wherein said first measurement set of electrodes includes a first and second electrode and a third center electrode wherein the center electrode is used as a reference electrode for each of the other electrodes of said first measurement set of electrodes.

4. The method of claim 1 wherein said first measurement set of electrodes lies on a meridian of said blood exclusion volume proximate the equator of said blood exclusion body.

5. The method of claim 1 further comprising the following steps:

incrementing the location of said index set of electrodes and repeating said steps until all measurement sets of electrodes have been indexed.

6. The method of claim 5 further comprising the following steps:

displaying on the display means a value representing the volume of said heart from said distance measures.

7. The method of claim 5 further comprising the following steps:

displaying on the display means a value representing the motion of the heart wall from said distance measures.

* * * * *